United States Patent [19]

Portney et al.

[11] Patent Number: 5,179,262
[45] Date of Patent: Jan. 12, 1993

[54] MANUFACTURE OF OPHTHALMIC LENSES BY EXCIMER LASER

[75] Inventors: Valdemar Portney, Irvine; Albert C. Ting, Laguna Niguel; Timothy R. Willis, Lake Forest, all of Calif.

[73] Assignee: Allergan, Inc., Irvine, Calif.

[21] Appl. No.: 730,684

[22] Filed: Jul. 16, 1991

Related U.S. Application Data

[60] Division of Ser. No. 323,493, Mar. 14, 1989, Pat. No. 5,053,171, which is a continuation-in-part of Ser. No. 919,206, Oct. 14, 1986, Pat. No. 4,842,782.

[51] Int. Cl.⁵ ............................................. B23K 26/00
[52] U.S. Cl. ........................... 219/121.68; 219/121.75
[58] Field of Search .................... 219/121.68, 121.69, 219/121.7, 121.71; 606/4, 5; 128/395

[56] References Cited

U.S. PATENT DOCUMENTS

| | | | |
|---|---|---|---|
| 3,410,203 | 11/1968 | Fischbeck | 101/1 |
| 3,440,388 | 4/1969 | Otstot et al. | 219/69 |
| 3,549,733 | 12/1970 | Caddell | 264/25 |
| 3,657,085 | 4/1972 | Hoffmeister et al. | 204/157.1 R |
| 3,742,182 | 6/1973 | Saunders | 219/121.85 |
| 3,915,609 | 10/1975 | Robinson | 425/174.6 |
| 3,972,599 | 8/1976 | Engel et al. | 350/294 |
| 4,017,233 | 4/1977 | Robinson | 425/174.6 |
| 4,032,861 | 6/1977 | Rothrock | 219/121.6 X |
| 4,081,655 | 3/1978 | Gale | 219/121.85 |
| 4,108,659 | 8/1978 | Dini | 346/76 L X |
| 4,128,752 | 12/1978 | Gravel | 219/121.6 |
| 4,147,402 | 4/1979 | Chown | 219/121.85 X |
| 4,194,814 | 3/1980 | Fischer et al. | 346/76 L X |
| 4,219,721 | 8/1980 | Kamen et al. | 219/121.85 |
| 4,275,288 | 6/1981 | Makosch et al. | 219/121.75 |
| 4,307,046 | 12/1981 | Neefe | 219/121.66 |
| 4,323,317 | 4/1982 | Hasegawa | 219/121.6 |
| 4,328,411 | 5/1982 | Haller et al. | 219/121.67 X |
| 4,370,175 | 1/1983 | Levatter | 219/121.73 X |
| 4,402,579 | 9/1983 | Poler | 351/160 R |
| 4,414,059 | 11/1983 | Blum et al. | 219/121.85 |
| 4,430,548 | 2/1984 | Macken | 219/121.67 |
| 4,450,593 | 5/1984 | Poler | 351/160 R |
| 4,455,893 | 6/1984 | Astero | 219/121.65 X |
| 4,473,735 | 9/1984 | Steffen | 219/121.66 |
| 4,510,005 | 4/1985 | Nijman | 219/121.85 X |
| 4,556,524 | 12/1985 | Cullis et al. | 219/121.66 |
| 4,563,565 | 1/1986 | Kampfer et al. | 219/121.69 |
| 4,642,439 | 2/1987 | Miller et al. | 219/121.72 |
| 4,644,130 | 2/1987 | Bachmann | 219/121.69 |
| 4,652,721 | 3/1987 | Miller et al. | 219/121.67 |
| 4,665,913 | 5/1987 | L'Esperance, Jr. | 210/121.69 X |
| 4,669,466 | 6/1987 | L'Esperance | 364/413 X |
| 4,684,436 | 8/1987 | Burns et al. | 156/643 |

(List continued on next page.)

FOREIGN PATENT DOCUMENTS

| | | | |
|---|---|---|---|
| 1038935 | 9/1978 | Canada | 219/121.78 |
| 2546692 | 4/1977 | Fed. Rep. of Germany | |
| 2510768 | 7/1982 | France | |
| 29627 | 2/1983 | Japan | |
| 97787 | 6/1984 | Japan | |
| WO7/05496 | 9/1987 | PCT Int'l Appl. | |

OTHER PUBLICATIONS

"Laser Applications in Semiconductor Microlithography"; Kanti Jain; Lasers & Applications; Sep. 1983 pp. 49–56.

"Effective deep ultraviolet photoetching of polymethyl methacrylate by an excimer laser"; Y. Kawamura, K. Toyoda and S. Namba; Appl. Phys. Lett. 40(5), Mar. 1, 1982; pp. 374–375.

"Deep-ultraviolet spatial-period division using an excimer laser"; A. M. Hawryluk and Henry I. Smith;

(List continued on next page.)

*Primary Examiner*—C. L. Albritton
*Attorney, Agent, or Firm*—Gordon L. Peterson

[57] ABSTRACT

Complex small objects such as ophthalmic lenses are quickly and accurately fabricated from plastic or glass blanks of ablatable material such as plastic or glass by cutting, shaping, and radiusing the blank entirely by laser light, using appropriate masks with focusing and imaging optics.

25 Claims, 2 Drawing Sheets

U.S. PATENT DOCUMENTS

| | | | |
|---|---|---|---|
| 4,718,418 | 1/1988 | L'Esperance, Jr. | 219/121.68 |
| 4,721,379 | 1/1988 | L'Esperance, Jr. | 351/212 X |
| 4,729,372 | 3/1988 | L'Esperance, Jr. | 219/121.67 X |
| 4,732,148 | 3/1988 | L'Esperance, Jr. | 219/121.67 X |
| 4,770,172 | 9/1988 | L'Esperance, Jr. | 606/5 |
| 4,773,414 | 9/1988 | L'Esperance, Jr. | 606/5 |
| 4,798,204 | 1/1989 | L'Esperance, Jr. | 606/5 |
| 4,842,782 | 6/1989 | Portney et al. | 264/1.4 |
| 4,856,513 | 8/1989 | Muller | 219/121.6 X |
| 4,879,451 | 10/1989 | Gart | 219/121.69 |
| 4,915,981 | 4/1990 | Traskos et al. | 427/53.1 |
| 4,940,881 | 7/1990 | Sheets | 219/121.69 |
| 5,061,840 | 10/1991 | Portney et al. | 219/121.68 |

OTHER PUBLICATIONS

Optic Letters; vol. 7, No. 9 Sep. 1983; pp. 402–404.

"Laser Ablation of Organic Polymers: Microscopic Models For Photochemical and Thermal Processes"; B. Garrison et al, Journal of Applied Physics, 57(8); Apr. 15, 1985; pp. 2909–2914.

"Kinetics of the Ablative Photodecomposition of Organic Polymers in the Far-Ultraviolet (193nm)"; IBM Thomas J. Watson Research Center; pp. 1–11.

"Action of Far-Ultraviolet Light on Organic Polymer Films: Applications to Semiconductor Technology" IBM Thomas J. Watson Research Center; pp. 1–9.

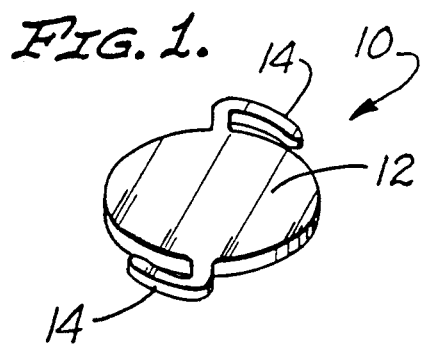
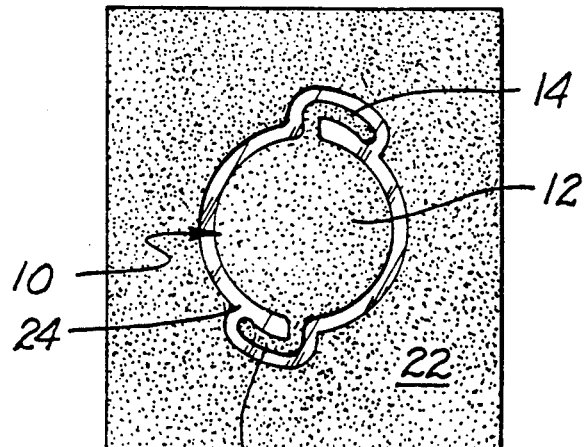
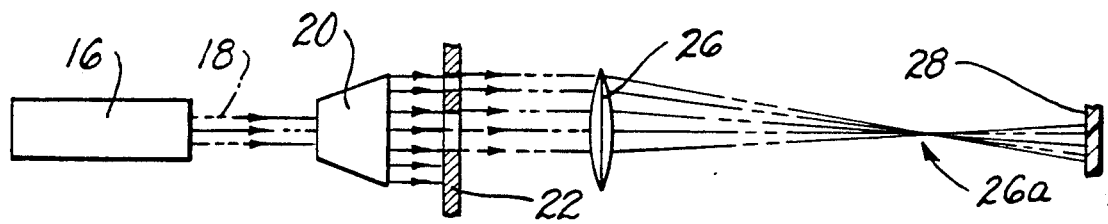
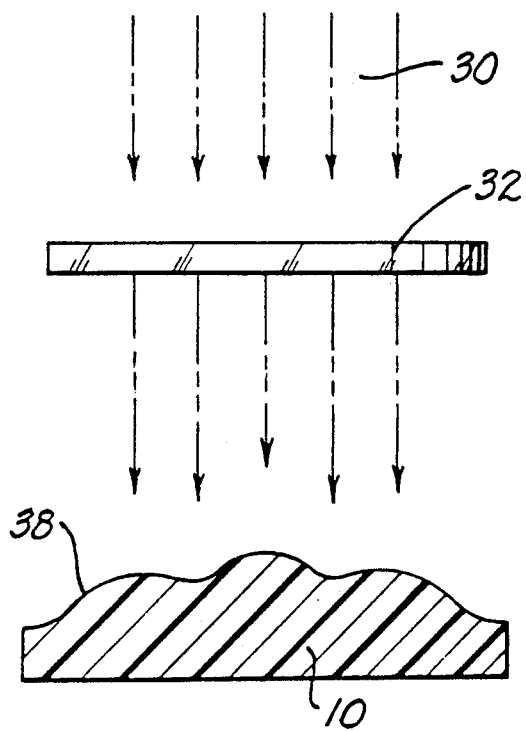
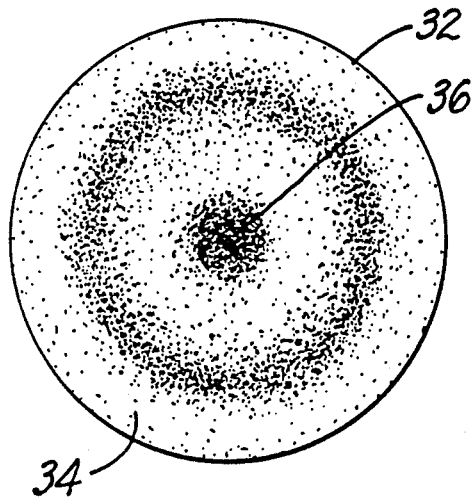

MANUFACTURE OF OPHTHALMIC LENSES BY EXCIMER LASER

This application is a division of application Ser. No. 323,493, filed Mar. 15, 1989, now U.S. Pat. No. 5,053,171 which is a CIP of Ser. No. 919,206 filed Oct. 4, 1986 now U.S. Pat. No. 4,842,782.

BACKGROUND OF THE INVENTION

1. Technical Field

The invention relates generally to the manufacture of ophthalmic lenses such as contact, corneal implant, and intraocular lenses, and other small plastic or glass objects of similar shape, and more particularly to a method of making such lenses or objects with a high degree of precision at low cost by using an excimer laser.

2. Background Information

Ophthalmic lenses are normally manufactured by a mechanical process in which a block of polymehthylmethacrylate (PMMA) is machined while being adhesively held on a support. The machining is quite difficult because of the small size of the lens and the intricacy of the shape into which the lens must be machined.

Typically, three operations must be performed to shape a lens. For one, the workpiece must be cut out from a blank to form, for example, an integral optic and haptic. In addition, the surface of the workpiece must be machined to the desired optical specifications, which may include convexities or concavities of varying radii at different points on the surface of the lens, and the edges of the workpiece must be radiused or rounded.

In the prior art, the edge rounding step alone typically required 7-14 days of gemstone tumbling, and precision was hard to accomplish in all of the steps.

SUMMARY OF THE INVENTION

The present invention provides a method of fabricating ophthalmic lenses or similar small objects quickly and accurately by using a laser, and particularly an excimer laser, to cut, surface-model, and bevel a workpiece which is preferably made of PMMA but may, for appropriate purposes, be made of other plastics or of glass. The type and tuning of the laser is dependent upon the material of the blank.

In accordance with the invention, the workpiece is first cut to shape by shining a laser beam through a mask outlining the form of the cut required to shape (in the case of an ophthalmic lens) the optic and haptic. Considerable precision can be obtained in this step by expanding the laser beam in front of the mask and then reducing it beyond the mask to provide fine detail from a relatively large mask. The depth of the cut can be controlled by the number and energy of the pulses.

The surface modeling of the lens is next achieved by masking a laser beam in such a way that its energy distribution varies across the surface of the workpiece so as to ablate it to differing degrees at different points of the surface. This can be achieved by using a mask of varying opacity or a semi-transparent mirror with a coating of varying thickness at different points on the surface. This step, if desired, may be performed before the cutting step.

Finally, a laser beam is masked and focused generally into the form of a hollow cone whose tip is the focal point of the beam. By exposing the workpiece to the beam on one side of the focal point and then on the other, two bevel cuts are made along the perimeter of the upper and lower surfaces, respectively, of the workpiece. When combined with a vertical section of the side of the workpiece, these bevel cuts form an approximation of a rounded edge which is further softened by the slight melting of the workpiece material produced by the heat generated by the laser during cutting.

It is therefore the object of the invention to quickly and accurately produce a complex small object such as an ophthalmic lens from a blank entirely by the use of a laser.

According to another aspect of the invention, the method is modified in order to alleviate two concerns. One concern is that shining or projecting the laser beam through the mask toward the workpiece can be accompanied by some diffraction that may result in some distortion at the workpiece that can degrade resolution. Another concern is that mask size may have to approximate workpiece size and the laser beam may have to be expanded to cover the entire mask and the workpiece surface.

These problems are solved by adding the step of imaging to the step of laser beam projection previously described. In other words, a lens of one or more optical elements disposed intermediate the mask and the workpiece images the mask (i.e., the pattern on the mask) onto the workpiece. Better resolution can be had, mask size can be reduced, and beam expansion can be eliminated.

Generally, a method of making small objects from a blank of ablatable material according to this aspect of the invention includes at least one of the steps of (1) cutting a workpiece from the blank by exposing the blank to laser light in the outline of said workpiece without focusing the laser light at the workpiece, (2) exposing the surface of said workpiece to laser light through a mask having areas transmitting said light in varying degrees, and (3) shaping the edges of said workpiece by exposing them to an inclined beam of laser light, that step being performed so that it includes imaging the outline or pattern on the blank to achieve the advantages described above.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 is a perspective view of an intraocular lens to be manufactured by the method of this invention;

FIG. 2 is a schematic diagram of a laser optic used in the cutting step of the invention;

FIG. 3 a plan view of the mask used in the cutting step;

FIG. 4 is a schematic diagram illustrating the surface modeling step of this invention;

FIG. 5 is a plan view of the mask used in the surface modeling step;

DESCRIPTION OF THE PREFERRED EMBODIMENTS

Figure 6:
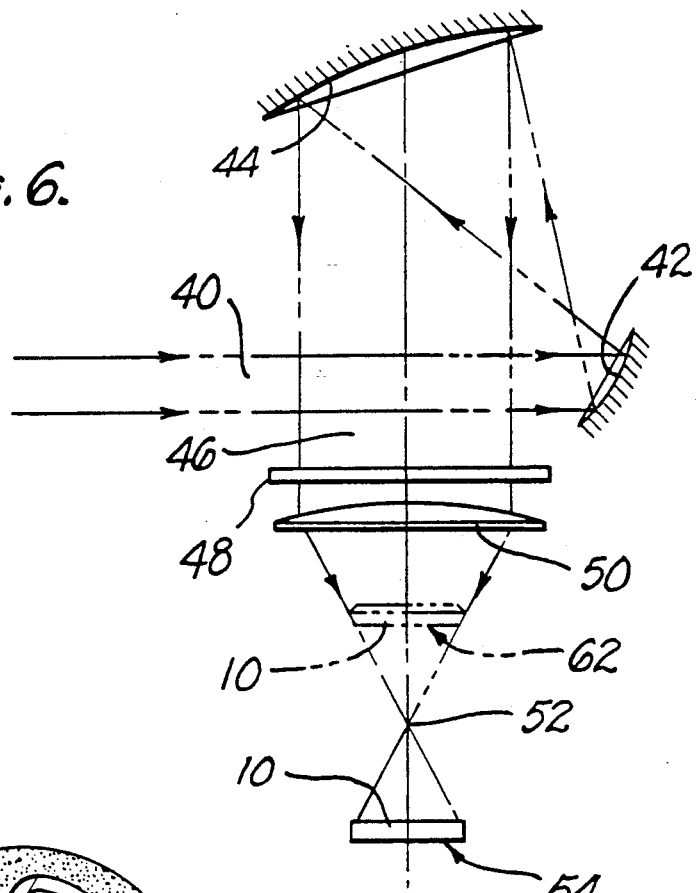
FIG. 6 is a schematic diagram illustrating the edge beveling step of this invention.

In the preferred embodiment of the invention, which is the manufacture of ophthalmic lenses from a PMMA blank, the method of this invention is carried out with an excimer laser, that is a laser operating in the high ultraviolet wavelengths. An argon-fluoride laser operating at a wavelength of 193 nm in 250 millijoule pulses is preferred, but broadly any ultraviolet wavelength substantially absorbed by the material of the workpiece may be used. The choice of the laser is dictated by its ability to break up the large molecules of the workpiece material (as in the case of plastic) or to melt the material (as in the case of glass) so that the material will ablate.

FIG. 1 shows a typical intraocular lens which may be produced by the method of this invention. The workpiece 10 has an optic 12 which forms the actual lens, and a haptic 14 by which the lens is anchored in the patient's eye. In the prior art, polypropylene is usually used for the haptic 14, and PMMA is used for the optic 12. However, both the optic 12 and the haptic 14 may be formed of PMMA, and in the process of this invention this is preferable because the entire workpiece can be cut as a single piece. Of course, other ultraviolet-absorbing materials than PMMA (e.g. silicone) may be used for the workpiece if they are medically acceptable and properly ablatable.

FIG. 2 shows an arrangement useful in cutting the workpiece 10 from a block of PMMA. An excimer laser 16 emits a beam 18 of coherent ultraviolet light. Because the diameter of beam 18 is fairly small, a conventional laser beam expander 20 is used to expand the beam 18 to a diameter of several centimeters. A mask 22 best shown in FIG. 3 is formed integrally with the beam expander 20 or placed into the path of the expanded beam 18 to allow only a narrow strip of light in the shape of the outline 24 of the workpiece 10 to pass through the mask 22.

A beam converger or focusing optic 26 is used to project a reduced image of the outline 24 onto the PMMA block 28. Repeated pulses of the laser 16 will ablate the material of the block 28 until the profiled lens or workpiece 10 is very precisely cut out of the block 28. The precision of the cut is enhanced (and the power density of the beam increased) by the use of a relatively large mask 22 and a substantial reduction of the mask image on the block 28.

Alternatively, the focusing optic 26 (which in this embodiment is a biconvex optical element) can include a lens of one or more elements configured according to known techniques to image the outline 24 on the block 28. In other words, the step of cutting a workpiece from said blank includes imaging the outline of said workpiece on said blank. This results in the beam having a focal point 26a intermediate the focusing optic 26 and the block 28 and, preferably, it is done so that the beam expander 20 is not needed and can be omitted.

After being cut out from the block 28, the workpiece 10 is placed into the path of an excimer laser beam 30 (FIG. 4) which has a uniform energy distribution across its area. A mask 32 is interposed between the workpiece 10 and the beam 32.

As best shown in FIG. 5, the mask 32 has different degrees of transparency at different points on the mask 32. For example, the mask 32 may have a coating of variable or non-uniform transmission characteristics, or it may be a neutral density filter (such as a polarizing or haze filter) with non-uniform transmission characteristics. In any event, the mask 32 transmits a large amount of beam energy in the areas 34 corresponding to desired depressions in the workpiece 10, and a small amount in the areas 36 corresponding to desired protrusions in the workpiece 10.

By appropriately controlling the transmission characteristics of the mask 32, it is possible to model or shape the surface 38 of the workpiece 10 in any desired manner without complex machining, and to do so precisely in a small amount of time. An imaging optic arrangement 32a (FIG. 4) can be located intermediate the mask 32 and the workpiece 10 in order to image the mask 32 (i.e., the pattern on the mask) on the workpiece 10. In other words, the step of exposing the surface of said workpiece to laser light includes imaging the mask on said workpiece. Such an imaging optic arrangement 32a includes a lens of one or more elements configured according to known techniques to have a focal point 32b intermediate the imaging optic arrangement 32a and the workpiece 10 in order to image the mask 32 (i.e., the pattern on the mask 32) on the workpiece 10, and imaging in this way achieves the advantages previously mentioned. The mask 32 can be combined with the mask 22 to conduct shaping and cutting simultaneously.

In an alternative embodiment of the invention, the mask 32 may take the form of a semi-transparent mirror with a reflective coating whose thickness varies along its surface. In that embodiment, the laser energy not used for ablation is reflected away from the workpiece.

After the shaping or modeling step of FIGS. 4 and 5, the workpiece is fully formed but has sharp vertical edges which are not suitable for intraocular use. In the prior art, the edges of the workpiece were radiused or rounded by gemstone tumbling for 7-14 days, but besides being time-consuming, this prior art method often defeated the carefully achieved precision of the workpiece.

In accordance with the invention, an excimer laser beam 40 (FIG. 6) is expanded by a beam expander or (preferably) by a pair of curved mirrors 42 and 44. The use of reflective rather than refractive beam expanding optics is preferred because it permits higher power transfer with smaller optics while avoiding damage to the optics.

Figure 7:
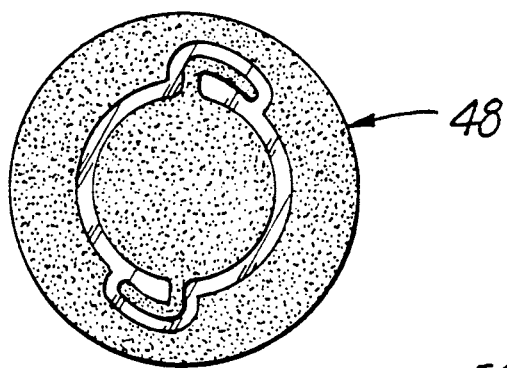
FIG. 7 is a plan view of the mask used in the beveling step.

The expanded beam 46 is conducted through a mask 48 best shown in FIG. 7 to a focusing lens 50. As a result, a beam generally in the form of a hollow cone is produced, with the tip of the cone being the focal point 52. The beveling of one side can be achieved during the cutting operation to expedite the overall process.

Figure 8:
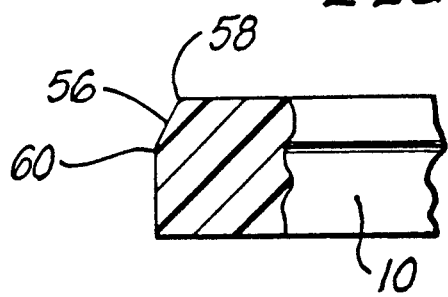
FIG. 8 is a fragmentary detail section of the workpiece after the first beveling step.

In order to round its edges, the workpiece 10 is first positioned below the focal point 52 at 54, and the laser is turned on. The conical shape of the beam will produce a bevel 56 (FIG. 8) on the edges of the workpiece 10, the focusing lens 50 being configured to image the mask 48 on the workpiece 10. The ends of the bevel 56 are slightly rounded at 58 and 60 by the small amount of heat which is produced during the ablation of workpiece material which forms the bevel 56.

Figure 9:
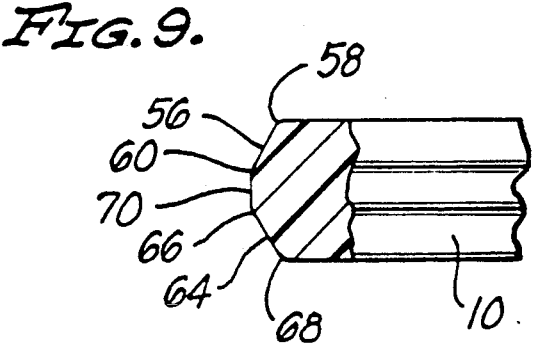
FIG. 9 is a fragmentary detail section of the workpiece after the second beveling step.

When the bevel 56 has been fully formed, the workpiece 10 is positioned above the focal point 52 at 62, and the beam is turned on again. This time, the conical shape of the beam results in cutting a bevel 64 (FIG. 9) whose edges are slightly rounded at 66 and 68 for the same reason as described above.

When combined with the vertical surface 70, the bevels 56 and 64 and their rounded extremities provide a sufficient approximation of a rounded edge for the workpiece 10 to make it suitable for implantation in a patient's eye without danger of irritation.

It will be seen that the above-described process provides a fast and accurate way of manufacturing intraocular lenses without the use of complex machining equipment. The invention can, of course, be carried out with variations. For example, a very narrow laser beam may be moved around the periphery of the workpiece in the cutting and beveling steps, rather than cutting or beveling the entire periphery at once, or a mask may be scanned rather than being exposed all at once.

Although an exemplary embodiment of the invention has been shown and described, many changes, modifications, and substitutions may be made by one having ordinary skill in the art without necessarily departing from the spirit and scope of the invention. For example, many of the steps in the following claims can be combined and such combinations are intended to fall within the scope of the claims.

What is claimed is:

1. An apparatus comprising:
   a mask;
   a laser for directing laser energy toward the mask with the laser energy being unfocused at the mask;
   the mask having variable transmissivity or reflectivity characteristics to the laser energy to provide a first laser beam of variable energy across its width; and
   means for imaging the mask on a surface so that the laser beam of variable energy is directed against the surface to remove material from multiple locations on the surface in accordance with said characteristics with more of the material being removed at one of the locations than is removed at another of the locations.

2. An apparatus as defined in claim 1 wherein the surface is on a workpiece and said characteristics shape the surface of the workpiece into an ophthalmic lens.

3. An apparatus as defined in claim 1 wherein said characteristics of the mask curve said surface.

4. An apparatus as defined in claim 1 wherein the surface is on a workpiece, and said characteristics of the mask shape the surface into a lens surface.

5. An apparatus as defined in claim 1 wherein said characteristics of the mask are such that said multiple locations are contiguous.

6. An apparatus as defined in claim 1 wherein the laser is an excimer laser.

7. An apparatus as define din claim 1 wherein the surface is on a workpiece and the apparatus includes means for cutting the workpiece from a blank by exposing the blank to laser energy int eh outline of said workpiece.

8. An apparatus as defined in claim 1 wherein the surface is on a workpiece and the apparatus includes means for directing a second laser beam toward a blank in a pattern without focusing eh second laser beam at the bland for a sufficient length of time to cut the workpiece form the blank.

9. An apparatus as defined in claim 8 wherein the means for directing the second laser beam toward the blank includes a second mask and means for directing the second laser beam through the second mask with the second laser beam passing through the second mask being in said pattern.

10. An apparatus as define din claim 8 including means for beveling an edges of the workpiece by exposing it to laser energy.

11. An apparatus as defined in claim 10 including a third mask and means for directing laser energy toward the third mask to the workpiece without focusing the laser energy at the workpiece to bevel and edge of the workpiece.

12. An apparatus as defined in claim 1 wherein the surface is on a workpiece and the apparatus includes means for beveling an edge of the workpiece by exposing it to laser energy.

13. An apparatus as defined in claim 1 wherein the surface is on a workpiece and the apparatus includes a second mask and means for directing laser energy toward the second mask to the workpiece without focusing the laser energy at the workpiece to bevel and edge of the workpiece.

14. An apparatus for cutting a workpiece from an object, said apparatus comprising:
    a mask having a pattern through which laser energy can pass, said pattern being in the outline of the workpiece;
    a laser for directing laser energy through the mask with the laser energy passing through the mask being in said pattern and being unfocused at the mask; and
    means for imaging the mask on the object whereby the laser energy can cut the workpiece int he shape of said pattern from the object.

15. An apparatus as defined in claim 15 including means for beveling an edge of the workpiece by exposing it to laser energy.

16. An apparatus as define din claim 15 including a second mask and means for directing laser energy toward the second mask to the workpiece without focusing the laser energy at the workpiece to bevel an edge of the workpiece.

17. An apparatus as defined in claim 14 wherein said pattern is generally in the shape of an intraocular lens.

18. An apparatus as defined in claim 14 wherein the means for imaging includes a lens between the mask and the object for focusing the laser energy at a location between the mask and the object.

19. An apparatus as defined din claim 14 including a beam expander between the laser and the mask and the laser energy between the beam expander and the mask is collimated.

20. An apparatus as defined in claim 14 including a beam expander between the laser and the mask and there are no lenses in the path of the laser energy between the beam expander and the mask.

21. Apparatus for beveling the edges of an object comprising:
    a laser for providing a beam of laser energy;
    a mask disposed in said beam to provide a masked laser beam, said mask having a central non-laser energy-transmitting area in the shape of the object; and
    means for directing the masked beam toward a focus which is intermediate the directing means and the object with the edge of the masked beam being substantially coincident with the edge of the object to bevel the edge of the object.

22. An apparatus as defined in claim 21 wherein the laser is an excimer laser.

23. An apparatus as defined in claim 1 wherein the mask has variable transmissivity characteristics.

24. An apparatus as defined in claim 1 wherein the mask has variable reflectivity characteristics.

25. An apparatus, comprising:
an excimer laser arranged to emit a beam of laser energy along a path to a surface of a workpiece of ablatable material;
a mask having a pattern of variable transmissivity or reflectivity, which mask is disposed intermediate the excimer laser and the workpiece in said path; and
imaging means disposed intermediate the mask and the workpiece for imaging the pattern on the surface of the workpiece in order to ablatively photodecompose portions of the workpiece according to the pattern.

* * * * *

UNITED STATES PATENT AND TRADEMARK OFFICE
CERTIFICATE OF CORRECTION

PATENT NO. : 5,179,262
DATED : January 12, 1993
INVENTOR(S) : Valdemar Portney et al It is certified that error appears in the above-identified patent and that said Letters Patent is hereby corrected as shown below:

Column 1, line 8, change "October 4" to -- October 14 -- .

Column 5, line 52, change "define din" to -- defined in -- .

Column 5, line 55, change "int eh" to -- in the -- .

Column 5, line 60, change "eh" before "second" to -- the -- .

Column 5, line 61, change "bland" to -- blank -- .

Column 5, line 62, change "form" to -- from -- .

Column 6, line 1, change "define din" to -- defined in -- .

Column 6, line 2, change "edges" to -- edge -- .

Column 6, line 7, change "and edge" to -- an edge -- .

Column 6, line 17, change "and edge" to -- an edge -- .

Column 6, line 29, change "int he shape" to -- in the shape -- .

Column 6, line 31, change "15 including" to -- 14 including -- .

UNITED STATES PATENT AND TRADEMARK OFFICE
CERTIFICATE OF CORRECTION

PATENT NO. : 5,179,262

DATED : January 12, 1993

INVENTOR(S) : Valdemar Portney et al

It is certified that error appears in the above-identified patent and that said Letters Patent is hereby corrected as shown below:

Column 6, line 34, change "define din" to -- defined in -- .

Column 6, line 45, change "define din" to -- defined in -- .

Signed and Sealed this

Twenty-sixth Day of October, 1993

Attest:

BRUCE LEHMAN

*Attesting Officer*   *Commissioner of Patents and Trademarks*